(12) United States Patent
Suzuki

(10) Patent No.: US 7,789,822 B2
(45) Date of Patent: Sep. 7, 2010

(54) ENDOSCOPIC THERAPEUTIC INSTRUMENT, ENDOSCOPE, AND ENDOSCOPIC THERAPEUTIC SYSTEM

(75) Inventor: Keita Suzuki, Kokubunji (JP)

(73) Assignee: Olympus Corporation (JP)

(*) Notice: Subject to any disclaimer, the term of this patent is extended or adjusted under 35 U.S.C. 154(b) by 1560 days.

(21) Appl. No.: 11/049,544

(22) Filed: Feb. 2, 2005

(65) Prior Publication Data
US 2005/0250989 A1 Nov. 10, 2005

(30) Foreign Application Priority Data
Feb. 3, 2004 (JP) ............................. 2004-026774

(51) Int. Cl.
*A61B 1/00* (2006.01)
(52) U.S. Cl. .................. 600/104; 600/106; 600/114; 600/117; 600/118; 600/153; 606/1
(58) Field of Classification Search ............ 600/104, 600/106, 114
See application file for complete search history.

(56) References Cited

U.S. PATENT DOCUMENTS

| | | | | |
|---|---|---|---|---|
| 3,835,854 | A * | 9/1974 | Jewett | 604/159 |
| 4,397,091 | A * | 8/1983 | Gustavsson et al. | 33/732 |
| 4,616,648 | A * | 10/1986 | Simpson | 606/108 |
| 4,637,404 | A * | 1/1987 | Gessman | 607/126 |
| 5,064,415 | A * | 11/1991 | Walder et al. | 604/164.02 |
| 5,174,276 | A * | 12/1992 | Crockard | 600/104 |
| 5,339,799 | A * | 8/1994 | Kami et al. | 600/117 |
| 5,346,498 | A * | 9/1994 | Greelis et al. | 606/108 |
| 5,372,124 | A | 12/1994 | Takayama et al. | |
| 5,431,645 | A * | 7/1995 | Smith et al. | 606/1 |
| 5,683,413 | A | 11/1997 | Miyagi | |
| 5,931,833 | A * | 8/1999 | Silverstein | 606/1 |
| 6,152,918 | A * | 11/2000 | Padilla et al. | 606/15 |
| 6,210,398 | B1 | 4/2001 | Ouchi | |
| 6,358,199 | B1 * | 3/2002 | Pauker et al. | 600/114 |
| 6,514,261 | B1 * | 2/2003 | Randall et al. | 606/108 |
| 6,554,793 | B1 | 4/2003 | Pauker et al. | |
| 6,726,675 | B1 * | 4/2004 | Beyar | 604/510 |

(Continued)

FOREIGN PATENT DOCUMENTS

EP  0 888 750 A1  1/1999

(Continued)

OTHER PUBLICATIONS

Search Report from European Patent Office issued May 18, 2005 in connection with corresponding application No. EP 01 001 237.6-1526.

*Primary Examiner*—Matthew J Kasztejna
(74) *Attorney, Agent, or Firm*—Ostrolenk Faber LLP

(57) ABSTRACT

An endoscopic therapeutic instrument has a therapeutic section, a flexible transmission member which transmits operating driving forces to the therapeutic section by moving forwardly and reversely, and a sheath section in which the transmission member can move forwardly and reversely. A proximal side of this transmission member is connected to an operating tube section, and the therapeutic section is driven by forward and backward movements of the operating tube section. An endoscope having a channel into which the endoscopic therapeutic instrument is insertable, contains a mechanism for driving the sheath section and a mechanism for driving the operating tube section. The endoscope controls these mechanisms to cooperate with each other in controlling the endoscopic therapeutic instrument operations.

12 Claims, 19 Drawing Sheets

U.S. PATENT DOCUMENTS

| | | | |
|---|---|---|---|
| 7,294,135 B2 * | 11/2007 | Stephens et al. | 606/108 |
| 2001/0004676 A1 * | 6/2001 | Ouchi | 600/106 |
| 2001/0016804 A1 * | 8/2001 | Cunningham et al. | 703/7 |
| 2002/0013570 A1 | 1/2002 | Ruegg et al. | |

FOREIGN PATENT DOCUMENTS

| | | |
|---|---|---|
| JP | S57-117823 | 7/1982 |

* cited by examiner

ENDOSCOPIC THERAPEUTIC INSTRUMENT, ENDOSCOPE, AND ENDOSCOPIC THERAPEUTIC SYSTEM

CROSS-REFERENCE TO RELATED APPLICATION

This application is based upon and claims the benefit of priority from the prior Japanese Patent Application No. 2004-026774, filed Feb. 3, 2004, the entire contents of which application are incorporated herein by reference.

BACKGROUND OF THE INVENTION

1. Field of the Invention

The present invention relates to an endoscopic therapeutic instrument and to an endoscope, and to an endoscopic therapeutic system as well.

2. Description of the Related Art

In general, while an operator is treating a required area in the body of a patient or preparing an examination or the like of a living tissue by working from outside the body through an endoscope, the operator at times continuously uses, a plurality of endoscopic therapeutic instruments such as a needle-shaped scalpel, a grasp forceps, etc. In this case, the operator has conventionally performed an operation such as inserting a selected one of the therapeutic instruments into the body through a channel disposed in an inserting section of the endoscope, drawing the therapeutic instrument out of the body after performing a predetermined treatment, and again inserting the same or a different therapeutic instrument into the channel.

When this therapeutic instrument is to be inserted into the channel, the operator must carefully insert a long therapeutic instrument into a narrow channel from a forceps opening of the endoscope and is, therefore, required to perform time-consuming work, with great concentration.

For this reason, an endoscope equipped with an inserting/removing device which automatically inserts and removes a therapeutic instrument into and from a channel has been proposed, and is disclosed, for example, in FIG. 1 of JP-A-57-117823.

BRIEF SUMMARY OF THE DISCLOSURE

An endoscopic therapeutic instrument according to the invention includes a therapeutic section which performs treatment, a flexible transmission member which transmits an operating driving force to the therapeutic section by moving it forwardly and reversely, a flexible sheath section which covers the transmission member so as to permit the transmission member to move forwardly and reversely inside of the sheath section, and a flexible operating tube section which is disposed apart from the sheath section and is connected to and covers the transmission member.

By operating the operating tube section to move forwardly and reversely, it is possible to operate the transmission member to cause it to move forwardly and reversely with respect to the sheath section, making it possible to transmit the operating driving force to the therapeutic section. Owing to the presence of the sheath section, it is possible to restrict the movement of the endoscopic therapeutic instrument in an endoscope. Since the operating tube section can be operated to move forwardly and reversely with the movement of the sheath section in the endoscope being restricted, operating driving forces can be efficiently transmitted to the therapeutic section.

Preferably, in the endoscopic therapeutic instrument according to the invention, each of the transmission member, the operating tube section and the sheath section has an elongate shape and a size which can be accommodated within a channel of the endoscope. According to this construction, the operating tube section can be operated to drive the therapeutic section with the transmission member, with the operating tube section and the sheath section housed inside of the channel of the endoscope. Accordingly, it is not necessary for the operating tube section of the endoscopic therapeutic instrument to extend from the forceps opening of the endoscope, whereby there is no need for an assistant to operate the endoscopic therapeutic instrument separately from the main operator of the endoscope.

Preferably, in the endoscopic therapeutic instrument according to the invention, an elastic section is disposed between the sheath section and the operating tube section. The elastic section is preferably a spring.

In this endoscopic therapeutic instrument, when the sheath section and the operating tube section move away from each other, the distance therebetween can be restrained in a predetermined range by the restoring force of the elastic section. Accordingly, variations in the separation distance between the sheath section and the operating tube section can be restrained except when necessary. Thereby, it is possible to prevent the operating driving force from being transmitted to the therapeutic section.

Preferably, the sheath section and the elastic section and the operating tube section are integrally formed of one coiled wire, with the winding of the wire of the elastic section being more loose than the winding of the wire of the operating tube section.

The sheath section and the elastic section and the operating tube section can be integrally formed, to reduce the number of components of the therapeutic instrument to achieve further simplification.

Preferably, the therapeutic section is attachably and detachably supported on the tips of the respective transmission member and sheath section.

The endoscopic therapeutic instrument allows carrying out various types of treatments by replacing therapeutic sections.

Preferably, the outside diameter of the operating tube section and the outside diameter of the sheath section are different from each other.

Since there is a difference between the outside diameter of the operating tube section and the outside diameter of the sheath section, it is possible to easily detect the location of the operating tube section.

An endoscope according to the invention includes a channel through which an endoscopic therapeutic instrument can be inserted, a first forward/reverse mechanism which causes the sheath section to move in the channel forwardly and reversely in the axial direction of the channel, and a second forward/reverse mechanism which causes the operating tube section to move in the channel forwardly and reversely in the axial direction of the channel separately from the first forward/reverse mechanism.

In this endoscope, after the endoscopic therapeutic instrument is inserted into the channel, both the sheath section and the operating tube section can be moved forwardly and reversely by driving both the first forward/reverse mechanism and the second forward/reverse mechanism. In addition, operating driving forces can be transmitted to the therapeutic section by stopping the first forward/reverse mechanism and driving the second forward/reverse mechanism forwardly and reversely. Accordingly, inside of the channel of the endoscope, it is possible to move the endoscopic therapeutic instrument forwardly and reversely, as well as drive the therapeutic section. It is not necessary to extend the operating tube section of the endoscopic therapeutic instrument from the forceps opening of the endoscope. Thus, there is no need for an assistant to operate the endoscopic therapeutic instrument separately from operator of the endoscope.

Preferably, the first forward/reverse mechanism includes a first contact section which comes into contact with the sheath section and a first transport mechanism which transports the first contact section in the axial direction of the sheath section, and the second forward/reverse mechanism includes a second contact section which comes into contact with the operating tube section and a second transport mechanism which transports the second contact section in the axial direction of the operating tube section.

In this endo scope, the sheath section can be moved forwardly and reversely by transporting the first contact section in the axial direction of the sheath section by means of a first transport mechanism. In addition, the operating tube section can be moved forwardly and reversely by moving the second contact section in the axial direction of the operating tube section by means of the second transport mechanism. Accordingly, both the sheath section and the operating tube section can be moved forwardly and reversely by operating the respective transport mechanisms in the same direction at the same speed. In addition, when only the second transport mechanism is driven, the operating tube section can be operated to relatively move forwardly and reversely with respect to the sheath section, whereby the operating driving forces can be transmitted to the therapeutic section.

Preferably, the first transport mechanism is a first rotary driving mechanism having a first roller, the first contact section is a peripheral surface of the first roller, the second transport mechanism is a second rotary driving mechanism having a second roller, and the second contact section is a peripheral surface of the second roller.

In this endoscope, when the first roller is rotated by the first rotary mechanism, the peripheral surface of the first roller is brought into contact with the periphery of the sheath section, whereby the sheath section can be moved forwardly and reversely in the rotating direction of the first roller. In addition, when the second roller is rotated by the second rotary mechanism, the peripheral surface of the second roller is brought into contact with the periphery of the operating tube section, whereby the operating tube section can be moved forwardly and reversely in the rotating direction of the second roller.

An endoscopic therapeutic system according to the invention includes an endoscopic therapeutic instrument according to the invention, an endoscope according to the invention, and a control section which controls forward/reverse driving of each of the first forward/reverse mechanism and the second forward/reverse mechanism. The control section has a first mode for driving both the first forward/reverse mechanism and the second forward/reverse mechanism to cause both the sheath section and the operating tube section to move forwardly and reversely in the channel, and a second mode for stopping the first forward/reverse mechanism and driving the second forward/reverse mechanism to cause the operating tube section to move forwardly and reversely with respect to the sheath section.

When the control section is set to the first mode, both the first forward/reverse mechanism and the second forward/reverse mechanism are driven to cause both the sheath section and the operating tube section to move forwardly and reversely in the channel, whereby the therapeutic instrument can be moved forwardly and reversely in the channel. When the control section is set to the second mode, only the second forward/reverse mechanism is driven to cause the operating tube section to move forwardly and reversely with respect to the sheath section, whereby the operating driving forces can be fed to the therapeutic section via the transmission means.

Preferably, the control section detects a difference between the outside diameter of the sheath section and the outside diameter of the operating tube section by means of the second forward/reverse mechanism and switches from the first mode to the second mode.

In this endoscope, while the control section is moving both the sheath section and the operating tube section forwardly and reversely in the first mode, if the control section detects a difference in outside diameter between the sheath section and the operating tube section by means of the second forward/reverse mechanism, the control section switches to the second mode and drives only the second forward/reverse mechanism to cause the operating tube section to move forwardly and reversely with respect to the sheath section, whereby operating driving forces can be fed to the therapeutic section via the transmission means.

Preferably, the first forward/reverse mechanism and the second forward/reverse mechanism are disposed on a proximal side of a forceps opening of the endoscope.

When the therapeutic instrument is inserted into the channel from the forceps opening, even if the first forward/reverse mechanism and the second forward/reverse mechanism are not driven, the therapeutic instrument can be operated to move forwardly and reversely in the channel in a conventional manner. Accordingly, even a therapeutic instrument which is inferior in compression resistance can be inserted and removed without the need to bring the first contact section nor the second contact section into pressure contact with the sheath section.

Preferably, the first forward/reverse mechanism is disposed on a distal side of the forceps opening of the endoscope and the second forward/reverse mechanism is disposed on a proximal side of the forceps opening.

In this endoscopic therapeutic system, even a therapeutic instrument which is provided with a therapeutic instrument operating section like a conventional therapeutic instrument can be operated to move forwardly and reversely in the channel, by inserting the therapeutic instrument into the channel from the forceps opening and driving only the first forward/reverse mechanism.

Preferably, the first forward/reverse mechanism and the second forward/reverse mechanism are disposed on a distal side of the forceps opening of the endoscope.

In this endoscopic therapeutic system, the therapeutic instrument according to the invention can be inserted into the channel from the forceps opening and operated to move forwardly and reversely in the channel, and the therapeutic section can also be operated.

BRIEF DESCRIPTION OF THE SEVERAL VIEWS OF THE DRAWINGS

These and other features, aspects, and advantages of the apparatus and methods of the present invention will become better understood with regard to the following description, appended claims, and accompanying drawings where:

DETAILED DESCRIPTION OF PREFERRED EMBODIMENTS

Preferred embodiments of the invention will be described below with reference to the accompanying drawings.

Figure 1:
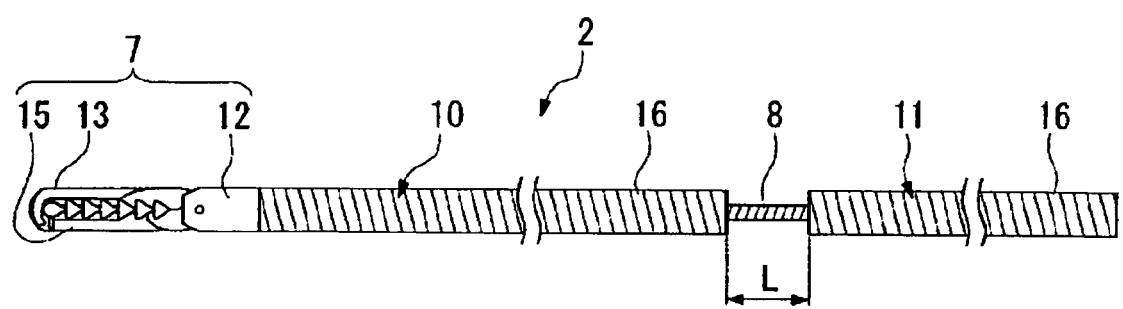
FIG. 1 is a side view showing a forceps according to a first embodiment of the invention.
Figure 2:
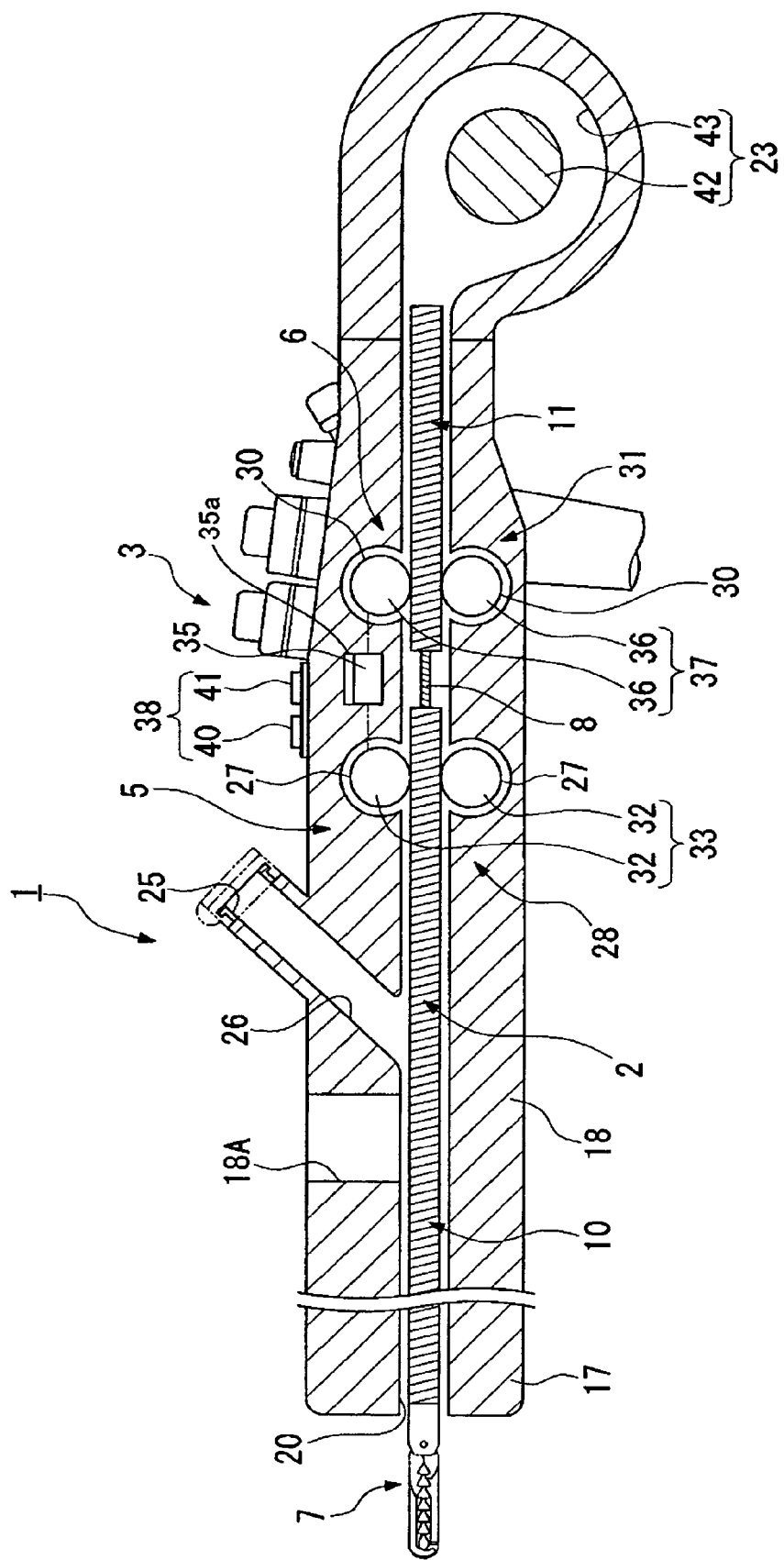
FIG. 2 is a partially cross-sectional side view showing an endoscopic therapeutic system according to the first embodiment of the invention.

A first embodiment according to the invention will be described below with reference to FIGS. 1 and 2.

An endoscopic therapeutic system 1 according to the first embodiment includes a forceps (an endoscopic therapeutic instrument) 2, an endoscope 3, and a control section 35a for controlling forward/reverse driving of each of a first forward/reverse mechanism 5 and a second forward/reverse mechanism 6, each of which will be described later. The control section (control means) is, for example, a CPU or a control electronic circuit.

The forceps 2 includes a therapeutic section 7 for administering treatments, a flexible operating wire (transmission means) 8 for transmitting operating driving forces to the therapeutic section 7 by forward/reverse movement, a flexible sheath section 10 which surrounds the operating wire 8, in a manner that permits the operating wire 8 to move forwardly and reversely inside the sheath section 10, and an operating tube section 11. The operating tube section 11 is disposed apart from the sheath section 10, and is connected to and receives the operating wire 8. The therapeutic section 7 includes a tubular tip cover member 12 connected to the tip of the sheath section 10, and a pair of openable and closable forceps halves 13 and 15 which are disposed at a position forward of the tip of cover member 12 and operable to open and close by forward and reverse movement of the operating wire 8.

The proximal side of the operating wire 8 projects from the proximal end of the sheath section 10, and is covered with the operating tube section 11 on a more proximal side from a position spaced apart from the proximal end of the sheath section 10 by at least a distance L which is provided for the forward/reverse operation of the operating wire 8.

Each of the sheath section 10 and the operating tube section 11 is integrally formed of one wire material 16, i.e. of a coiled, single wire which defines a flexible tubular body of a substantially constant diameter.

The endoscope 3 includes a flexible inserting section 17, an operating section 18 connected to the proximal end of the inserting section 17, and a channel 20 formed to place the inside of the inserting section 17 and the inside of the operating section 18 in communication with each other and to permit the forceps 2 to be inserted through. The endoscope 3 further includes the first forward/reverse mechanism 5 which causes the sheath section 10 to move in the channel 20 forwardly and reversely in the axial direction of the channel 20, the second forward/reverse mechanism 6 which causes the operating tube section 11 to move in the channel 20 forwardly and reversely in the axial direction of the channel 20 separately from the first forward/reverse mechanism 5, and a housing section 23 disposed at the proximal end of the operating section 18 and capable of housing the forceps 2.

A branch tube 26 which communicates with a forceps opening 25 in the operating section 18 is disposed in the channel 20.

The first forward/reverse mechanism 5 is disposed on a proximal side of the branch tube 26, and includes first contact sections 27 disposed in contact with the sheath section 10, and a first transport mechanism 28 for rotating the first contact sections 27 to feed the sheath section 10 in the axial direction.

The second forward/reverse mechanism 6 includes second contact sections 30 disposed in contact with the operating tube section 11, and a second transport mechanism 31 for rotating the second contact sections 30 to feed the operating tube section 11 in the axial direction, and is disposed on the proximal side of the branch tube 26 similarly to the first forward/reverse mechanism 5.

The first transport mechanism 28 is formed as a first rotary driving mechanism 33 having first rollers 32, and is connected to a driving section 35 such as a motor for rotationally driving the first rollers. The first contact sections 27 are respectively formed by the peripheral surfaces of the first rollers 32.

The second transport mechanism 31 is formed as a second rotary driving mechanism 37 having second rollers 36, and is the second contact sections 30 are respectively formed by the peripheral surfaces of the second rollers 36. The second rollers are connected to the driving section 35. The driving section 35 is connected to the first rollers 32 and the second rollers 36, and is capable of rotationally driving at least either of the first rollers 32 or the second rollers 36 by means of a switching mechanism (not shown).

The first rollers 32 and the second rollers 36 are respectively formed by pairs of rollers, and are opposed to each other so as to be brought into pressure contact with the sheath section 10 or the operating tube section 11 and are supported for rotation on their respective axes in the forward and reverse directions of the sheath section 10 or the operating tube section 11.

The first rollers 32 and the second rollers 36 are positioned in the operating section 18, and are disposed to be axially spaced apart from each other by at least the distance L at a more proximal position than is the branch tube 26.

The operating section 18 is provided with a switch 38 associated with the control section 35a and the driving section 35.

The switch 38 includes a forward/reverse switch 40 which can be switched to perform "forward", "reverse" and "stop" operations on the forceps 2 in the channel 20, and an opening/closing switch 41 which can be switched to "open" and "close" the forceps.

An opening 18A, which communicates with an intermediate section of the channel 20 on a distal side of the branch tube 26, is disposed on a side closer to the inserting section 17 than the branch tube 26.

The housing section 23 includes a cylindrical core section 42 and a passage 43 formed around the core section 42. The passage 43 is formed to allow insertion of the proximal side of the forceps 2 and to communicate with the channel 20, whereby the forceps 2 can be wound around the core section 42 on its proximal side.

The control section 35a has a first mode for driving both the first forward/reverse mechanism 5 and the second forward/reverse mechanism 6 to move both the sheath section 10 and the operating tube section 11 forwardly and reversely in the channel, and a second mode for stopping the first forward/reverse mechanism 5 and driving the second forward/reverse mechanism 6 to move the operating tube section 11 forwardly and reversely with respect to the sheath section 10.

The first mode is set by operating the forward/reverse switch 40, while the second mode is set by operating the opening/closing switch 41.

The operating method as well as the operation and the advantage of the endoscopic therapeutic system 1 according to the first embodiment will be described below with illustrative reference to a case where collecting foreign matter is carried out.

First, the inserting section 17 of the endoscope 3 is inserted into a body cavity.

Then, the therapeutic section 7 of the forceps 2 housed in the housing section 23 is drawn from the channel 20 and is brought into contact with the peripheral surfaces of the second rollers 36. Then, the forward/reverse switch 40 is set to "forward" to execute the first mode. Namely, the first rollers 32 and the second rollers 36 are made to rotate at the same speed in their rotating directions to urge the forceps 2 to move in the channel 20 toward the tip end thereof. During this time, the therapeutic section 7 and the sheath section 10 are sequentially drawn into the gap between the second rollers 36 and brought into pressure contact with the second rollers 36 so as to be transported toward the tip end of the channel 20, thus reaching the first rollers 32.

The therapeutic section 7 and the sheath section 10 are drawn into the gap between the first rollers 32 and are transported toward the tip end of the channel 20 by the operations of the first rollers 32 which are similar to those of the second rollers 36.

When the therapeutic section 7 is moved to a position in which it projects from the tip end of the channel 20 by a predetermined length, the forward/reverse switch 40 is switched to "stop", thereby stopping the rotations of the first rollers 32 and the second rollers 36.

At this position, the first rollers 32 are in a state of grasping the sheath section 10, while the second rollers 36 grasp the operating tube section 11.

Then, the opening/closing switch 41 is set to "open" to execute the second mode, in which only the second rollers 36 are made to rotate in the direction in which the operating tube section 11 is made to move toward the tip end of the channel 20 with respect to the sheath section 10. As a result, the operating wire 8 connected to the operating tube section 11 moves forwardly in the sheath section 10, exerting an axially directed force to the forceps halves 13 and 15, which causes the forceps halves 13 and 15 to open.

After the forceps halves 13 and 15 are positioned to grasp the foreign matter, the foreign matter is captured, by operating the opening/closing switch 41 to the "closed" position.

In this position of the switches, only the second rollers 36 rotate in the direction in which the operating tube section 11 is made to move with respect to the sheath section 10 toward the proximal end of the channel 20, and the operating wire 8 connected to the operating tube section 11 moves reversely in the sheath section 10. At this time, a force acting in the axial direction is transmitted to the forceps halves 13 and 15, whereby the forceps halves 13 and 15 are closed to grasp the foreign matter.

Then, the inserting section 17 of the endoscope 3 is removed from the body cavity and the foreign matter is collected.

After the foreign matter is collected, the forward/reverse switch 40 is switched to "reverse" to execute the first mode. Namely, the first rollers 32 and the second rollers 36 are made to rotate at the same speed in directions reverse to their forward rotating directions, and the sheath section 10, with which the first rollers 32 contact, and the operating tube section 11, with which the second rollers 36 contact, are made to move together toward the proximal end of the channel 20. During this time, since the rollers moving speeds are kept the same, the forceps 2 moves toward the proximal end in the channel 20.

At this time, the proximal side of the operating tube section 11 is inserted into the passage 43 and is wound around the core section 42, thereby being housed in the housing section 23.

Thus, in the endoscopic therapeutic system 1, during the first mode, since the first rollers 32 and the second rollers 36 are rotationally driven in the same direction with respect to the forceps 2 at the same speed, the sheath section 10 clamped between the peripheral surfaces of the first rollers 32 and the operating tube section 11 clamped between the peripheral surfaces of the second rollers 36, can be transported forwardly and reversely in the axial direction, which corresponds to the rotating directions of the first rollers 32 and the second rollers 36, whereby the forceps 2 can be moved forwardly and reversely in the channel 20.

During the second mode, since only the second rollers 36 are driven, the operating tube section 11 is relatively moved forwardly and reversely with respect to the sheath section 10, whereby operating driving force can be transmitted to the therapeutic section 7.

Furthermore, when the forceps 2 is inserted into the channel 20 from the forceps opening 25, the forceps 2 can be manually moved forwardly and reversely in the channel 20 in a conventional manner, even if the first rollers 32 and the second rollers 36 are not driven. Accordingly, the disclosed endoscope system allows even a therapeutic instrument such as a balloon which is not suitable for insertion or removal by rollers to be inserted into and removed from the channel 20 without the need to bring the first rollers 32, nor the second rollers 36, into pressure contact with the sheath section 10.

Figure 3:
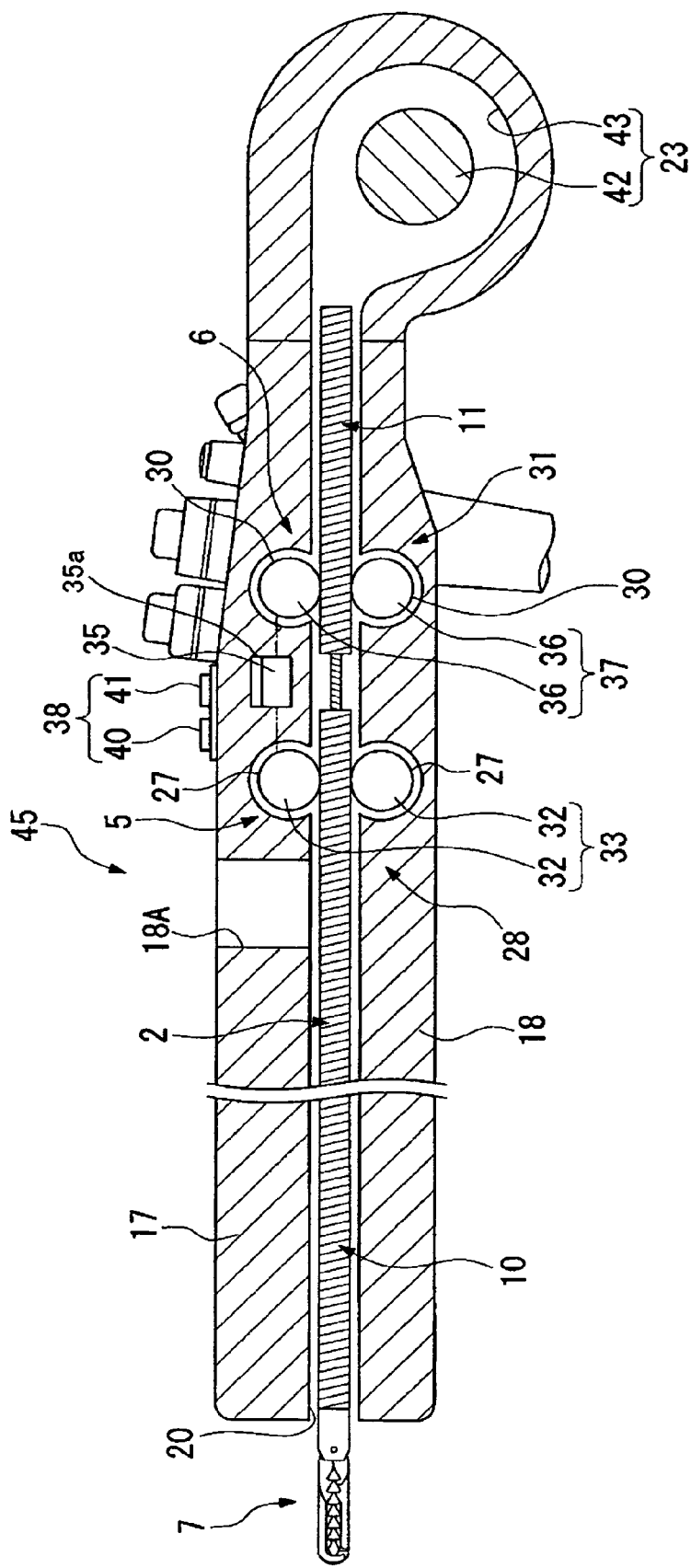
FIG. 3 is a partially cross-sectional side view showing an example of another endoscopic therapeutic system according to the first embodiment of the invention.

In addition, even with an endoscope 45 which, as shown in FIG. 3, does not have the forceps opening 25 nor the branch tube 26, the forceps 2 can be operated to move forwardly and reversely in the channel 20 and the forceps halves 13 and 15 can be automatically opened and closed.

Figure 4:
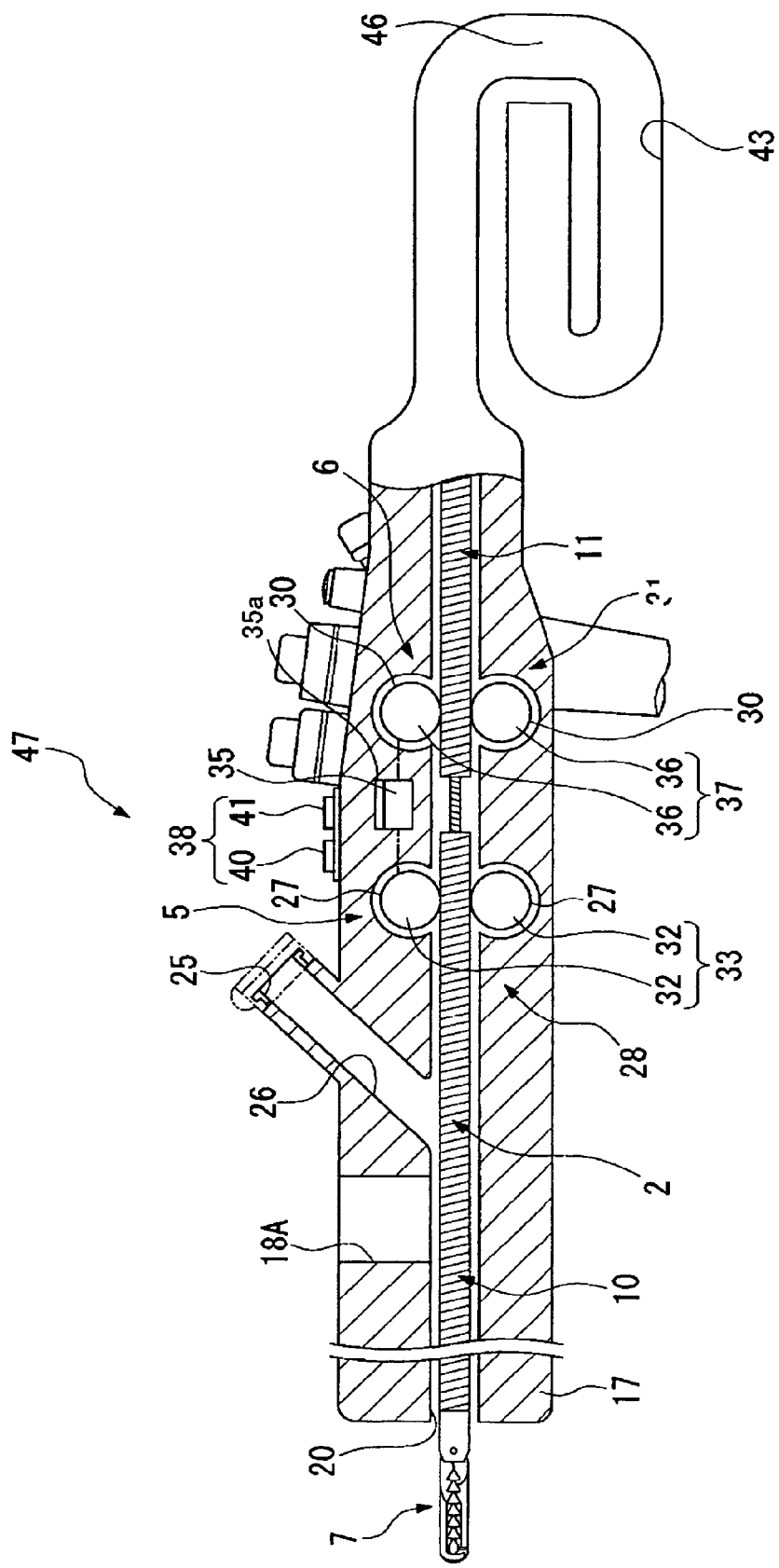
FIG. 4 is a partially cross-sectional side view showing an example of another endoscopic therapeutic system according to the first embodiment of the invention.

In addition, the first embodiment may also be applied to an endoscope 47 in FIG. 4 in which the housing section 46 does not have the core section 42 and is formed by only the passage 43 which is spirally constructed. In this case, since, the entire forceps 2 has flexibility, the entire forceps 2 can be compactly housed in the housing section 46.

Figure 5:
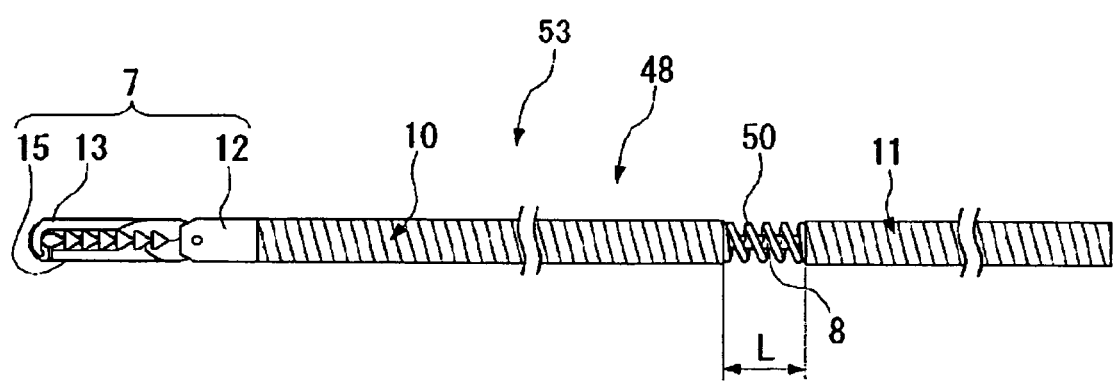
FIG. 5 is a side view showing a forceps according to a second embodiment of the invention.
Figure 6:
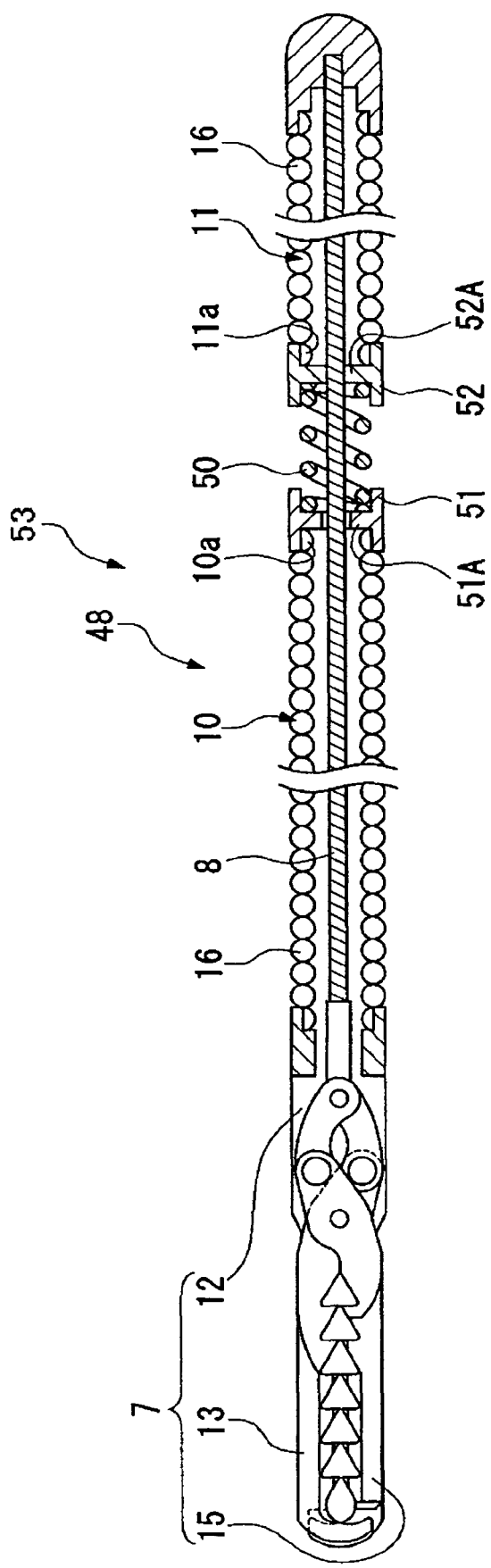
FIG. 6 is a cross-sectional view showing one side of the forceps according to the second embodiment of the invention.

A second embodiment will be described below with reference to FIGS. 5 and 6.

In the following description, the same reference numerals are used to denote constituent elements similar to those used in the above-described first embodiment, and the description thereof is omitted.

The second embodiment differs from the first embodiment in that a spring (elastic section) 50 is disposed between the operating tube section 11 and the sheath section 10 of a forceps 48 according to the second embodiment.

A distal-side short tube 51 having an inside peripheral surface from which a distal-side engagement section 51A projects radially inwardly is fixed to a proximal end 10a of the sheath section 10 by brazing, while a proximal-side short tube 52 having an inside peripheral surface from which a proximal-side engagement section 52A projects radially inwardly is fixed to a tip 11a of the operating tube section 11 by brazing. The spring 50 has approximately the same outside diameter as each of the distal-side short tube 51 and the proximal-side short tube 52, and is fixed by being clamped between the distal-side engagement section 51A and the proximal-side engagement section 52A.

The coils of the spring 50 are wound further apart as compared to the coils of the operating tube section 11 and the sheath section 10.

According to this endoscopic therapeutic system 53, it is possible to obtain similar effects and advantages by an operating method similar to that used in the first embodiment, and in addition, since the spring 50 is disposed, even if the proximal end 10a of the sheath section 10 and the tip 11a of the operating tube section 11 are to move close to each other, the distance therebetween can be restrained to a predetermined range by the restoring force of the spring 50. Accordingly, it is possible to prevent the problem that while an operator is operating the forceps 48 to cause it to move forwardly or reversely in the channel 20, the operating tube section 11 relatively moves with respect to the sheath section 10 and opens or closes the pair of forceps halves 13 and 15 against the operator's intention. In addition, even if a compressive force is applied to the operating wire 8 when the operating wire 8 is in, for example, a curved state, the buckling of the operating wire 8 can be prevented by the restoring force of the spring 50.

Figure 7:
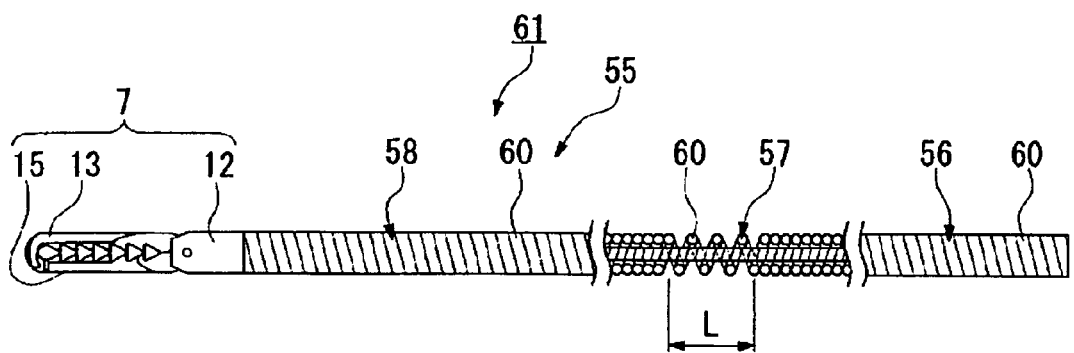
FIG. 7 is a partially cross-sectional side view showing a forceps according to a third embodiment of the invention.

A third embodiment will be described below with reference to FIG. 7.

In the following description, the same reference numerals are used to denote constituent elements similar to those used in the prior embodiments, and the description thereof is omitted.

The third embodiment differs from the second embodiment in that an operating tube section 56, a spring 57 and a sheath section 58 of a forceps 55 according to the third embodiment are integrally formed of one wire material 60 wound in a coiled form, and the winding of the wire material 60 of the spring 57 is looser than that of the wire material 60 of each of the operating tube section 56 and the sheath section 58.

According to this endoscopic therapeutic system 61, it is possible to obtain similar effects and advantages by an operating method similar to that used in the second embodiment, and in addition, the operating tube section 56, the spring 57 and the sheath section 58 can be integrally formed, whereby the number of components of the forceps 55 can be reduced to achieve further simplification.

Figure 8:
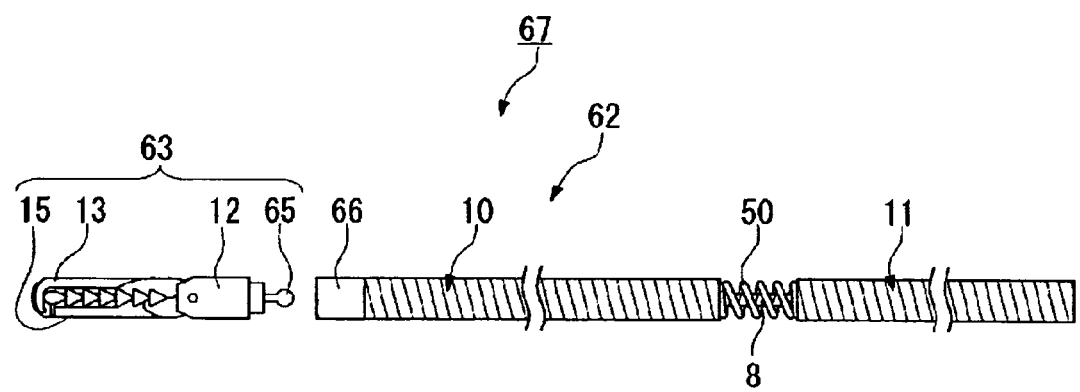
FIG. 8 is a partially cross-sectional side view showing a forceps according to a fourth embodiment of the invention.

A fourth embodiment will be described below with reference to FIG. 8.

In the following description, the same reference numerals are used to denote constituent elements similar to those used in the above embodiments, and the description thereof is omitted.

The fourth embodiment differs from any of the above-mentioned embodiments in that a therapeutic section 63 of a forceps 62 according to the fourth embodiment has a therapeutic-section-side attachment/detachment section 65 that can be detachably attached to the operating-side attachment/detachment section 66 provided at the tip of each of the sheath section 10 and the operating wire 8.

According to this endoscopic therapeutic system 67, it is possible to obtain similar effects and advantages by an operating method similar to that used in each of the prior embodiments, and in addition, unlike the related art, even if a long operating tube section or sheath section is not moved into and out of the endoscope, it is possible to easily replace therapeutic sections, whereby it is possible to carry out various types of treatments.

Figure 9:
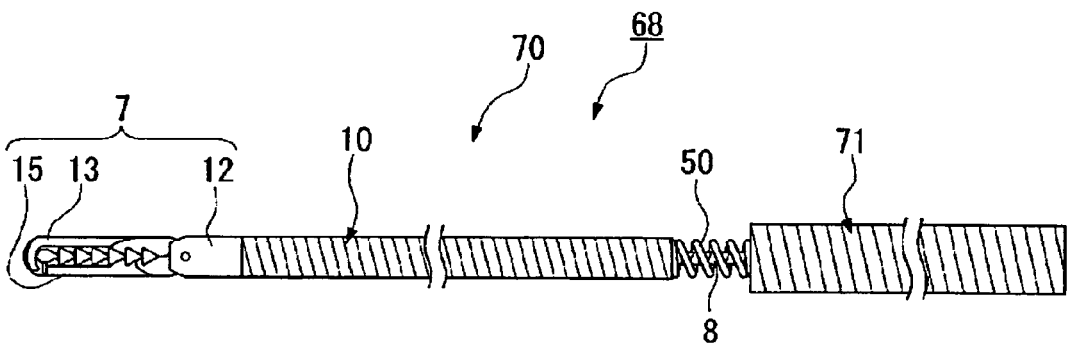
FIG. 9 is a side view showing a forceps according to a fifth embodiment of the invention.
Figure 10:
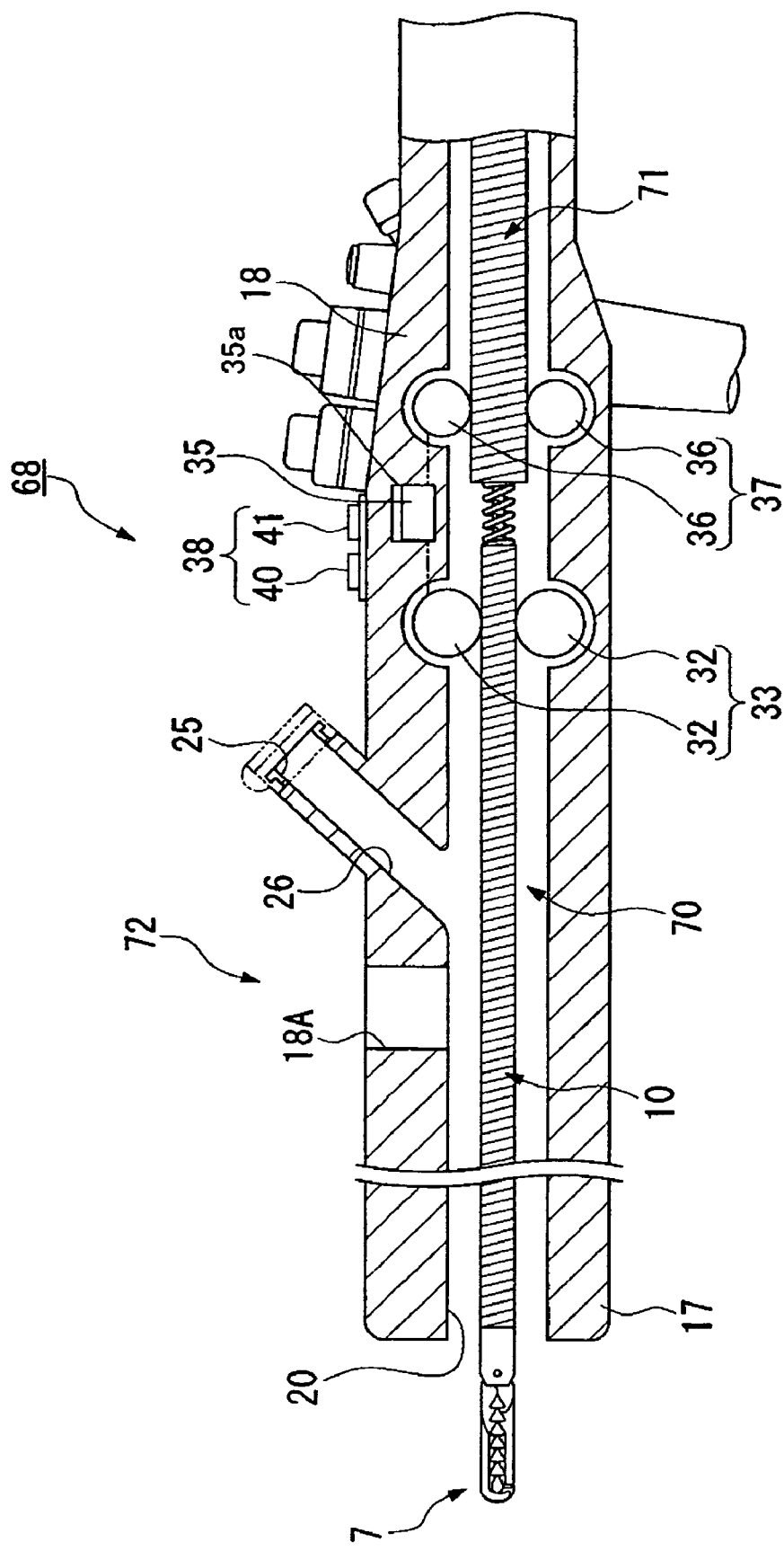
FIG. 10 is a partially cross-sectional side view showing an endoscopic therapeutic system according to the fifth embodiment of the invention.

A fifth embodiment will be described below with reference to FIGS. 9 and 10.

In the following description, the same reference numerals are used to denote constituent elements similar to those used in the above embodiments, and the description thereof is omitted.

The fifth embodiment differs from any of the above-mentioned embodiments in that the outside diameter of an operating tube section 71 of a forceps 70 in an endoscopic therapeutic system 68 according to the fifth embodiment is larger than the outside diameter of the sheath section 10.

Therefore, the distance between the second rollers 36 disposed in an endoscope 72 is larger than the distance between the first rollers 32.

The operating method as well as the operation and the advantage of this endoscopic therapeutic system 68 are described below.

First, both the first rollers 32 and the second rollers 36 are driven by an operation method similar to that used in the above-mentioned endoscopic therapeutic systems and the forceps 70 is inserted toward the tip end of the channel 20. At this time, even if the operating tube section 71 is moved to the position of the first rollers 32, the tip of the operating tube section 71 comes into abutment with the first rollers 32, thereby preventing further movement of the forceps 70.

Accordingly, it is possible to obtain advantages similar to those of the above-mentioned embodiments, and in addition, it is possible to prevent the forceps 70 from projecting in excess of a predetermined length outwardly from the tip end of the channel 20.

In addition, during insertion or removal, when the operating tube section 71 is placed at a position where it is out of pressure contact with the second rollers 36, the operating tube section 71 and the second rollers 36 are not brought into contact with each other, whereby the second rollers 36 need to be driven and far more power saving can be achieved.

Figure 11:
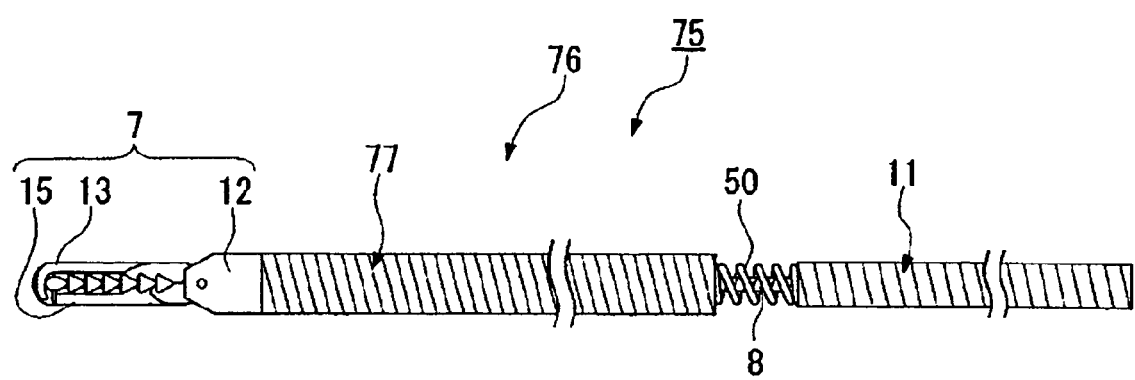
FIG. 11 is a side view showing a forceps according to a sixth embodiment of the invention.
Figure 12:
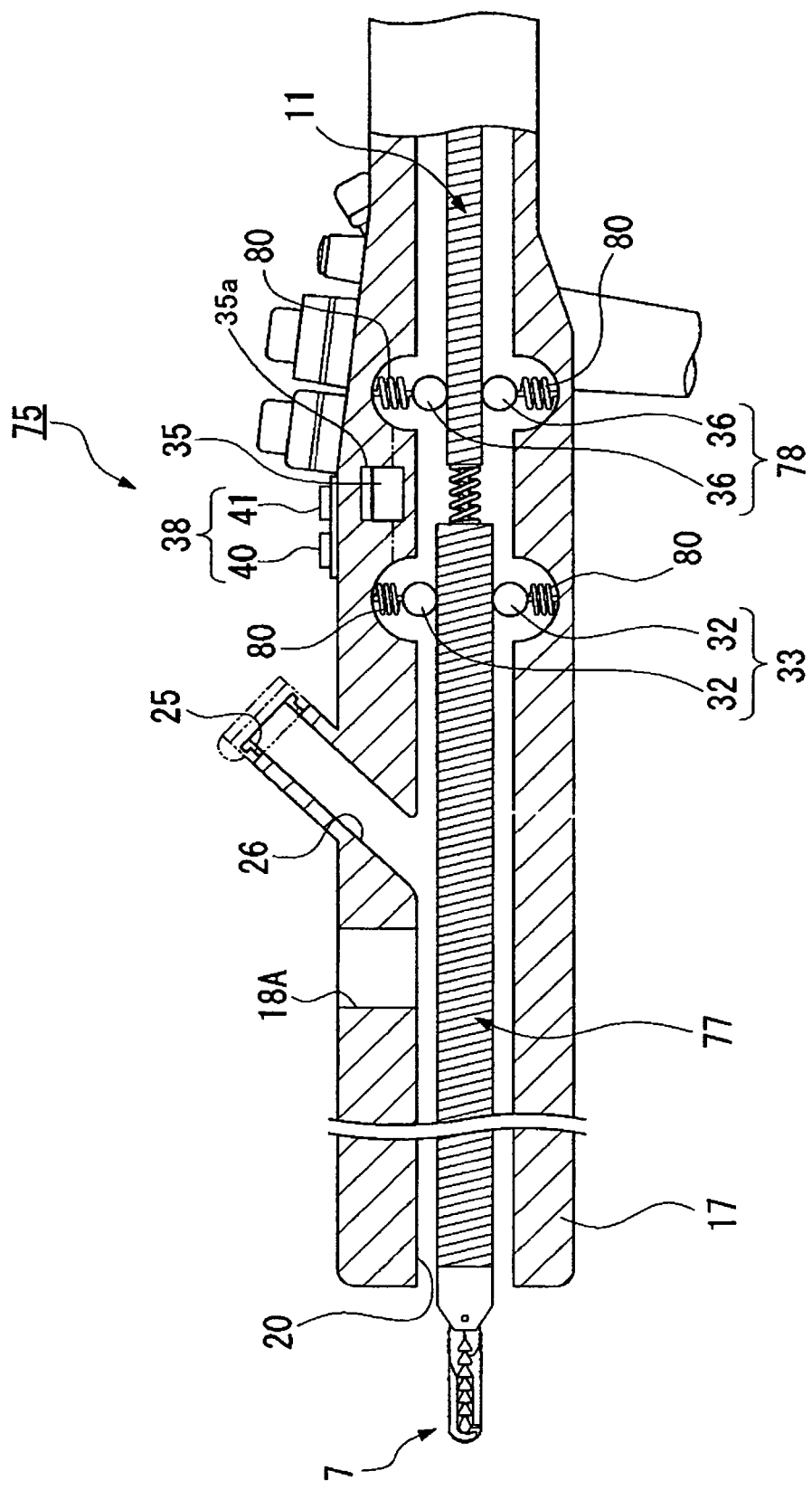
FIG. 12 is a partially cross-sectional side view showing an endoscopic therapeutic system according to the sixth embodiment of the invention.

A sixth embodiment will be described below with reference to FIGS. 11 and 12.

In the following description, the same reference numerals are used to denote constituent elements similar to those used in the above embodiments, and the description thereof is omitted.

The sixth embodiment differs from the fifth embodiment in that the outside diameter of the operating tube section 11 of a forceps 76 in an endoscopic therapeutic system 75 according to the sixth embodiment is larger than the outside diameter of a sheath section 77 and the control section 35a detects the difference between the outside diameter of the sheath section 77 and the outside diameter of the operating tube section 11 by means of a second forward/reverse mechanism 78 and automatically switches from the first mode to the second mode.

The first rollers 32 and the second rollers 36 are respectively supported by spring sections 80 so that the first rollers 32 can be moved toward and away from each other in the radial direction of the sheath section 77, while the second rollers 36 can be moved toward and away from each other in the radial direction of the operating tube section 11, whereby the contact pressure between the forceps 76 and each of the first rollers 32 and the second rollers 36 is adjusted by the expansion and contraction of the spring sections 80.

The spring sections 80 are connected to an encoder (not shown) connected to the control section 35a, and the encoder is constructed to be able to read displacement and variation of each of the spring sections 80.

The operating method as well as the operation and the advantage of this endoscopic therapeutic system 75 will be described below.

First, the forceps 76 is made to move in the channel 20 from a position where the second rollers 36 are brought into pressure contact with the sheath section 77 to a position where the second rollers 36 are brought into pressure contact with the operating tube section 11, by an operating method similar to that used in the above-described endoscopic therapeutic systems. When the second rollers 36 are brought into pressure contact with the operating tube section 11, the distance between the second rollers 36 is reduced and the spring sections 80 are expanded. When the encoder reads this expansion, the control section 35a detects that the second rollers 36 have been brought into pressure contact with the operating tube section 11. Then, after the lapse of a predetermined time, the control section 35a determines that the forceps 76 has advanced excessively in the channel 20, and stops the rotation of the driving section 35 even if the forward/reverse switch 40 is not operated.

With this endoscopic therapeutic system 75, it is possible to obtain advantages similar to those of the above-mentioned embodiments, and in addition, it is possible to prevent the forceps 70 from projecting excessively outwardly from the tip end of the channel 20 by erroneous operation.

Figure 13:
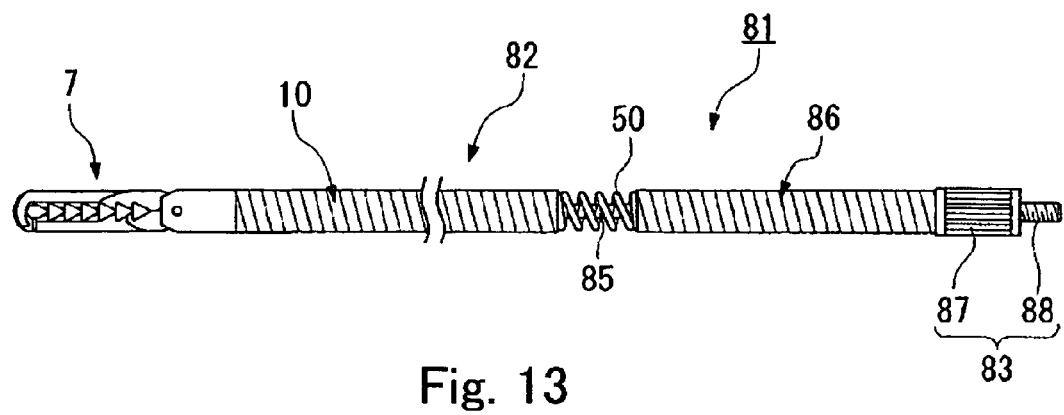
FIG. 13 is a side view showing a forceps according to a seventh embodiment of the invention.
Figure 14A:
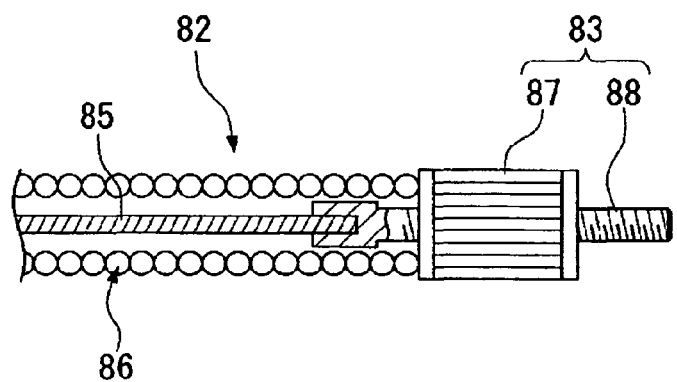
FIGS. 14A and 14B are partially cross-sectional, magnified side views showing main constituent elements of the forceps according to the seventh embodiment of the invention.
Figure 14B:
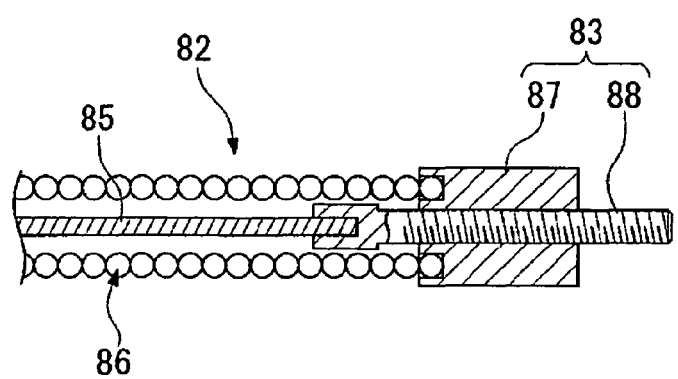

A seventh embodiment will be described below with reference to FIGS. 13, 14A and 14B.

In the following description, the same reference numerals are used to denote constituent elements similar to those used in the prior embodiments, and the description thereof is omitted.

The seventh embodiment differs from the second embodiment in that a forceps 82 of an endoscopic therapeutic system 81 according to the seventh embodiment includes an adjustment mechanism 83 capable of adjusting the amount of deformation of the spring 50 and an operating wire 85 is movable forwardly and reversely with respect to an operating tube section 86 even inside of the operating tube section 86.

The adjustment mechanism 83 includes a knob section 87 which is connected to the proximal end of the operating tube section 86 and has an internally threaded groove in its inside, and an adjustment section 88 which is connected to the proximal end of the operating wire 8 and further has an externally threaded groove on its peripheral surface and is screwed into the knob section 87.

With this endoscopic therapeutic system 81, the operating tube section 86 can be moved with respect to the operating wire 8 by the knob section 87 being rotated with respect to the adjustment section 88, whereby the spring 50 connected to the operating tube section 86 can be expanded or contracted to adjust the amount of biasing force acting to close the forceps halves 13 and 15.

Figure 15:
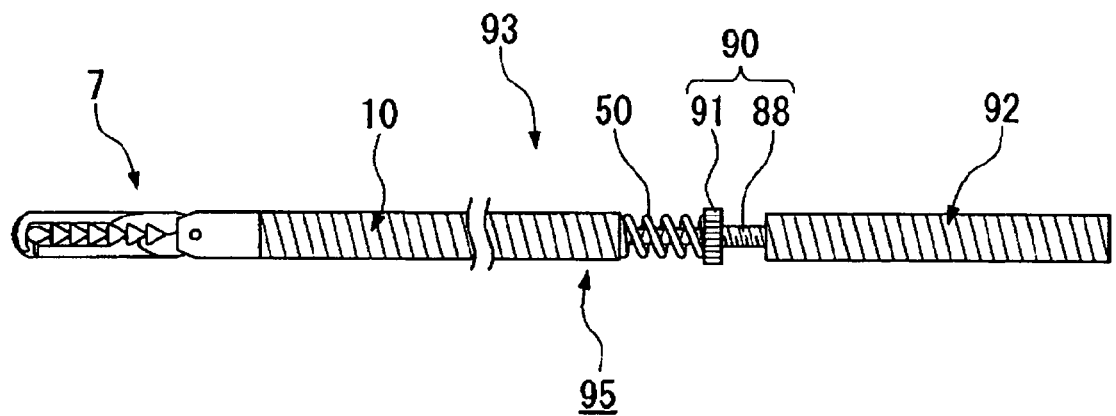
FIG. 15 is a side view showing a forceps according to another embodiment of the invention.
Figure 16:
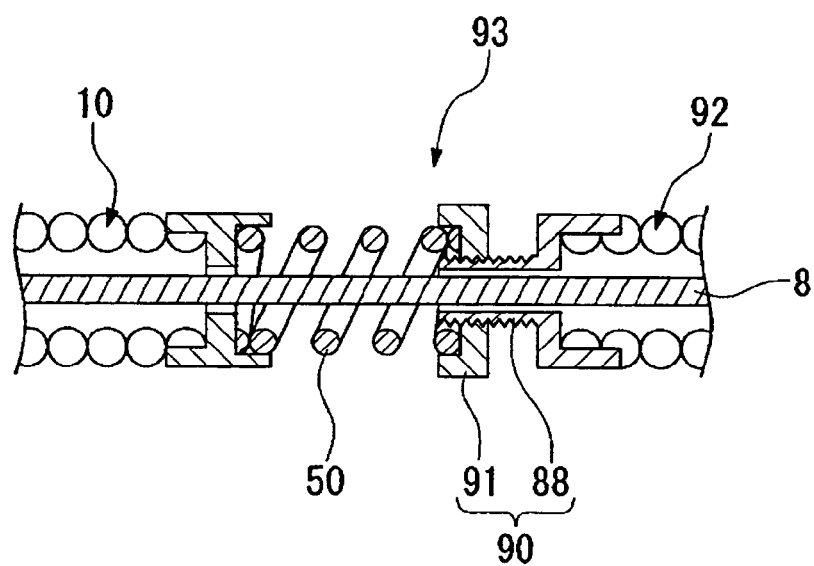
FIG. 16 is a partially cross-sectional, magnified side view showing main constituent elements of the forceps according to the embodiment of the invention shown in FIG. 15.
Figure 17:
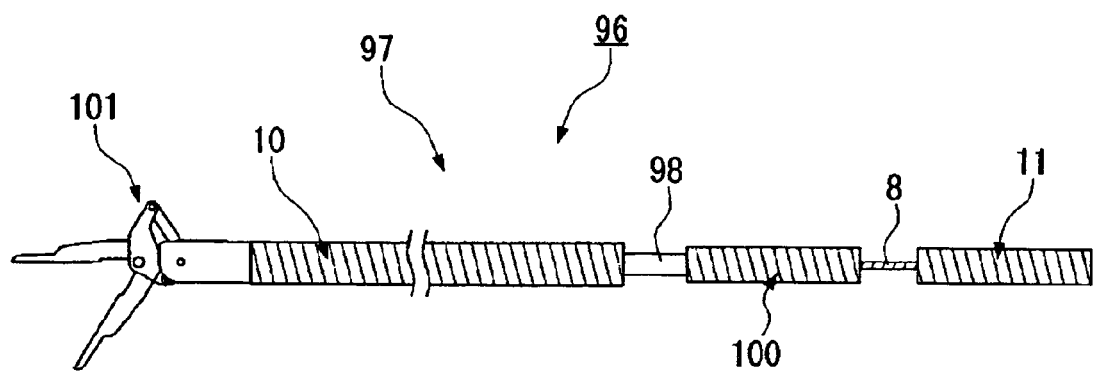
FIG. 17 is a side view showing a forceps according to an eighth embodiment of the invention.
Figure 18:
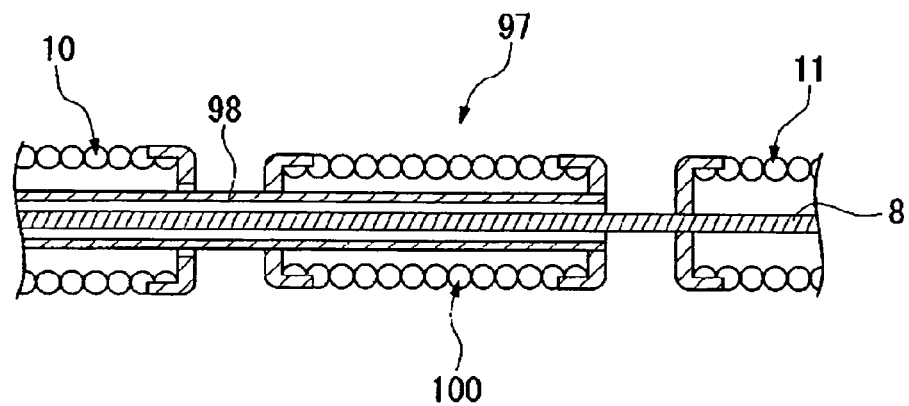
FIG. 18 is a magnified side view showing a cross section of the essential constituent elements of the forceps according to the eighth embodiment of the invention.

In addition, the seventh embodiment may also be applied to the forceps 93 shown in FIGS. 15 and 16 in which a knob section 91 of an adjustment mechanism 90 is connected to the proximal end of the spring 50 so that the knob section 91 can be rotated with respect to the spring 50, and the adjustment section 88 is connected to the tip of an operating tube section 92 so that the adjustment section 88 can be moved forwardly and reversely with respect to the operating wire 8.

According to this endoscopic therapeutic system 95, the distance between the tip of the operating tube section 11 and the proximal end of the spring 50 can be varied by the spring 50 being expanded and contacted by rotating the knob section 91, whereby it is possible to obtain advantages similar to those described above.

An eighth embodiment will be described below with reference to FIGS. 17 through 20.

In the following description, the same reference numerals are used to denote constituent elements similar to those used in the prior embodiments, and the description thereof is omitted.

The eighth embodiment differs from the first embodiment in that a multi-DOF (degrees-of-freedom) forceps, comprising an endoscopic therapeutic instrument 97 of an endoscopic therapeutic system 96 according to the eighth embodiment, includes a tube member 98 which covers the operating wire 8 so as to permit the operating wire 8 to move forwardly and reversely inside the tube member 98 and which can move forwardly and reversely in the sheath section 10, and a flexible open/close operating member 100 which is disposed between the sheath section 10 and the operating tube section 11 and is wound in a coiled form to cover the proximal side of the tube member 98.

A therapeutic section 101 includes a cover member 103 which is connected to the tip of the sheath section 10 and has a tip bifurcated by a slit 102, and forceps halves 105 and 106. The forceps halves 105 and 106 are pivoted in the slit 102 for rotation on the rotation axis of a first pivot member 107 disposed at the proximal end of the forceps half 105, and the forceps halve 106 is pivoted by the forceps half 105 so that the forceps half 106 can be opened and closed on the axis of a second pivot member 108.

The tip side of the tube member 98 is connected to a proximal section 110a of a deviation link member 110 which transmits the forward/reverse force of the tube member 98 to the therapeutic section 101, and a tip section 110b of the deviation link member 110 is connected to a first link member 111 which further transmits the transmitted force to the forceps half 106. The tip of the operating wire 8 is connected to a second link member 112 which further transmits the forward/reverse force of the operating wire 8 to the forceps half 105.

The deviation link member 110 has a tip side that extends parallel to the tube member 98 at a position offset from a central axis C of the tube member 98 in the radial outward direction thereof.

The forceps half 106 is rotatably connected to the first link member 111 via a third pivot member 113, while the deviation link member 110 is rotatably connected to the first link member 111 via a fourth pivot member 115.

The forceps half 105 is rotatably connected to the second link member 112 via a fifth pivot member 116, while the second link member 112 is rotatably connected to the operating wire 8 via a sixth pivot member 117.

An endoscope 118 includes third rollers 120 which are disposed between the first rollers 32 and the second rollers 36 and are formed by a pair of rollers opposed to each other so as to be brought into pressure contact with the open/close operating member 100 and which are also pivoted for rotation in the forward and reverse directions of the open/close operating member 100. The third rollers 120 are also connected to the driving section 35.

A swing switch 121 for causing the therapeutic section 101 to swing about the first pivot member 107 is disposed in an operating section 122.

When the forward/reverse switch 40 is set to "forward", the first rollers 32, the second rollers 36 and the third rollers 120 are made to rotate at the same speed in the same direction, while when the forward/reverse switch 40 is set to "reverse", the first rollers 32, the second rollers 36 and the third rollers 120 are made to rotate in directions opposite to their forward rotating directions. When the opening/closing switch 41 is operated, only the third rollers 120 are rotationally driven. When the swing switch 121 is operated, only the second rollers 36 are rotationally driven.

The operating method of the endoscopic therapeutic system 96 according to the eighth embodiment is described below.

First, the forceps halves 105 and 106 are inserted into the channel 20 in a closed state.

After the forceps halves 105 and 106 are inserted, the forward/reverse switch 40 is set to "forward" to cause the first rollers 32, the second rollers 36 and the third rollers 120 to rotate at the same speed in the same direction, thereby moving the multi-DOF forceps 97 forwardly in the channel 20.

When the multi-DOF forceps 97 is moved to a position where the first rollers 32 are brought in pressure contact with the sheath section 10, the second rollers 36 are brought in pressure contact with the operating tube section 11, and the third rollers 120 are brought in pressure contact with the open/close operating member 100, the forward/reverse switch 40 is switched to "stop" to stop the movement of the multi-DOF forceps 97.

If the forceps halves 105 and 106 are to be opened in this state, the opening/closing switch 41 is switched to "open" to rotationally drive only the third rollers 120 in the direction in which the open/close operating member 100 is made to advance in the channel 20 toward the tip end thereof.

Figure 19:
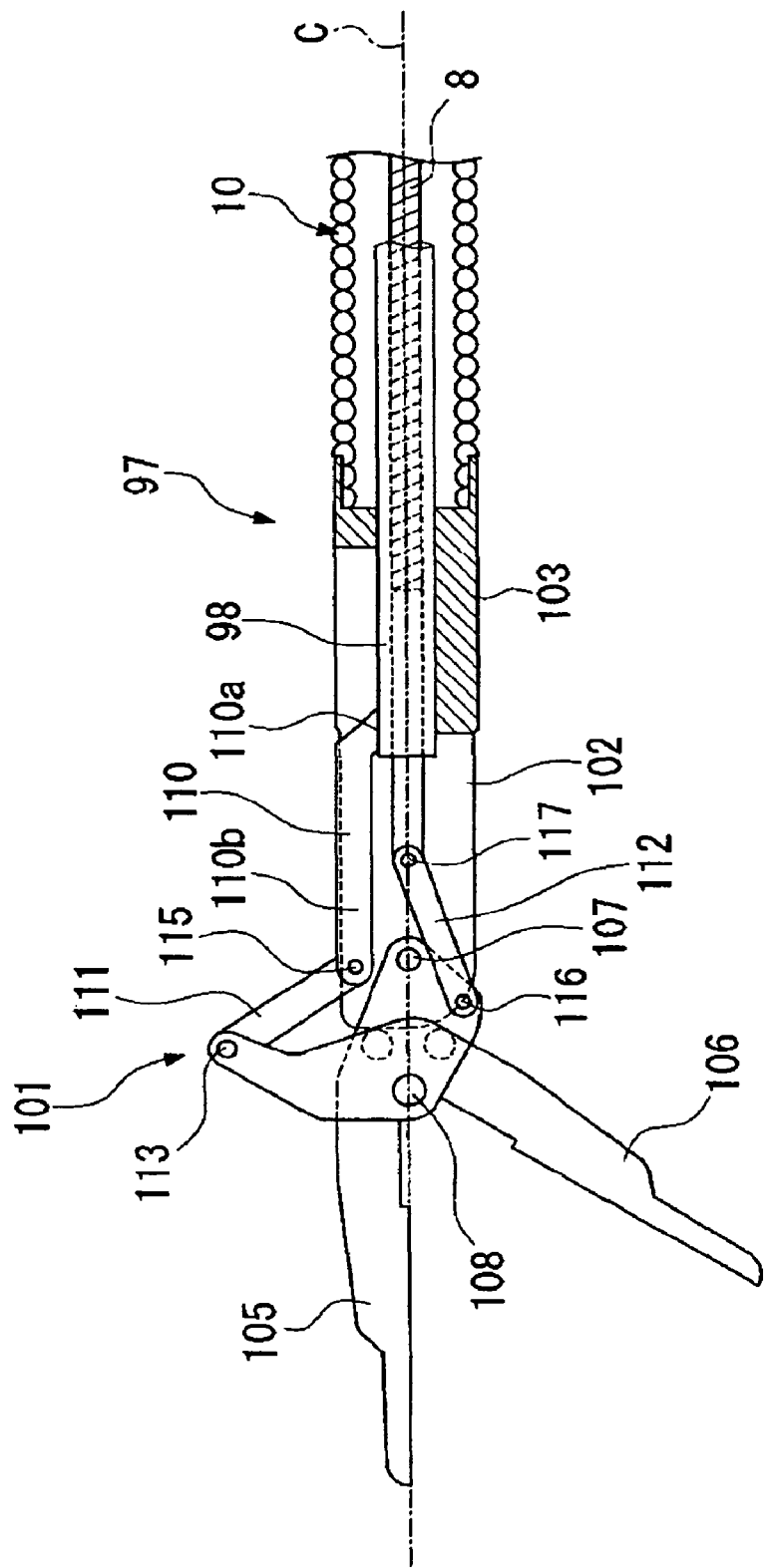
FIG. 19 is a partially cross-sectional side view showing the forceps according to the eighth embodiment of the invention.
Figure 20:
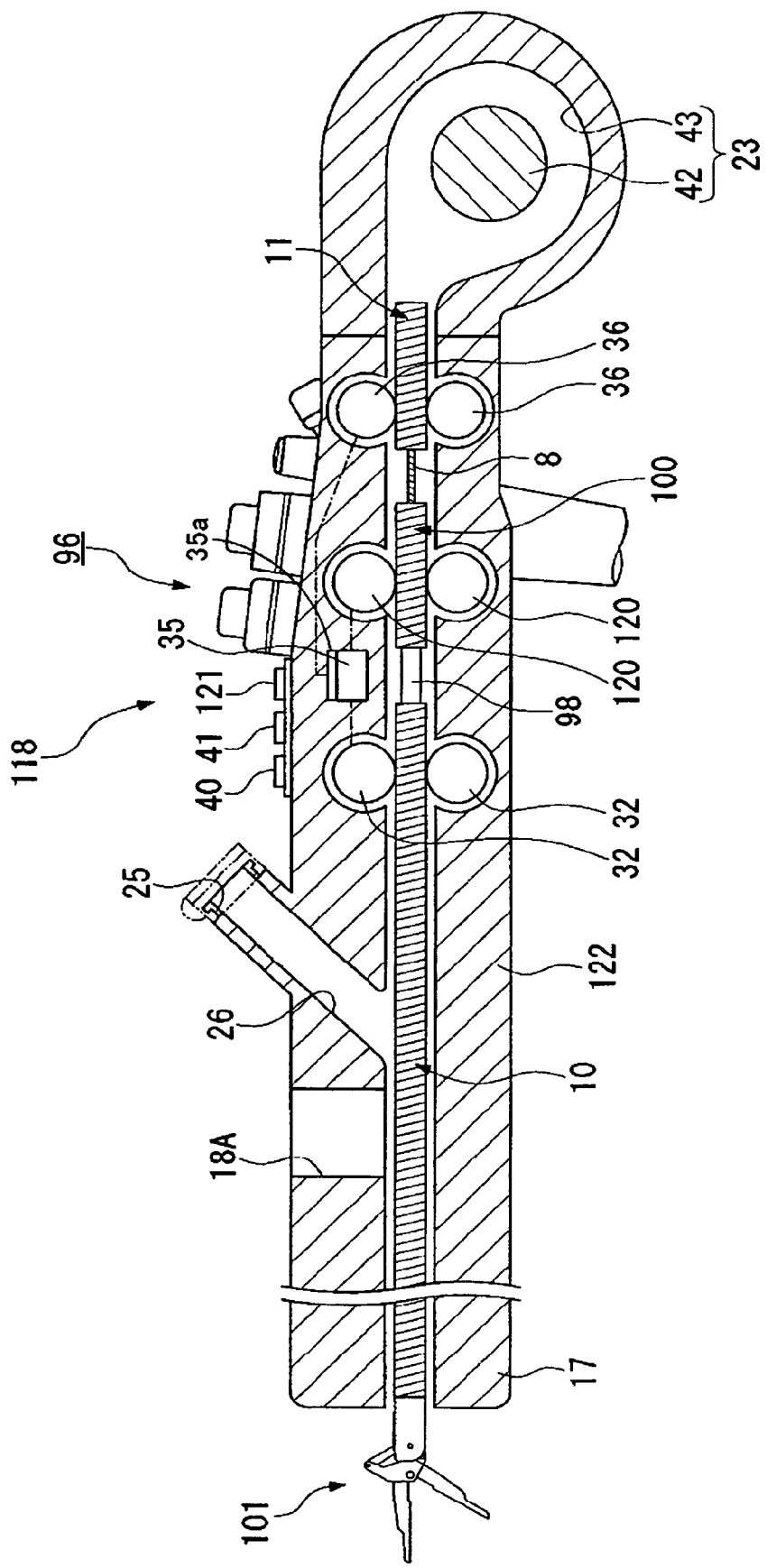
FIG. 20 is a partially cross-sectional side view showing an endoscopic therapeutic system according to the eighth embodiment of the invention.

At this time, the deviation link member 110 connected to the open/close operating member 100 moves to the tip side of the cover member 103 to cause the first link member 111 to rotate on the fourth pivot member 115 in the clockwise direction as viewed in FIG. 19, thereby applying rotational torque to the third pivot member 113 to cause the forceps half 106 to rotate on the second pivot member 108 in the counterclockwise direction as viewed in FIG. 19. In this manner, the pair of forceps halves 105 and 106 is opened.

When the opening/closing switch 41 is switched to "close", the third rollers 120 are rotationally driven in the opposite direction to cause the opening/closing member 100 to move in the opposite direction, thereby closing the forceps halves 105 and 106.

When the forceps halves 105 and 106 are to be swung, the swing switch 121 is operated to rotationally drive only the second rollers 36 in the direction in which the operating tube section 11 is made to move reversely in the channel 20 toward the proximal side thereof.

At this time, the operating wire 8 and the second link member 112 connected to the operating wire 8 move reversely. Accordingly, the fifth pivot member 116 rotates about the first pivot member 107 and moves toward a more proximal side than the position of the first pivot member 107, thereby transmitting rotational torque to the forceps half 105.

In this manner, the forceps half 105 together with the forceps half 106 is rotated toward the second link member 112 on the central axis of the first pivot member 107.

When the forceps are to be returned to the original state, the swing switch 121 is operated to rotationally drive the second rollers 36 in the direction reverse to the above-mentioned one to move the operating tube section 11 in the opposite direction, thereby rotating the forceps halves 105 and 106.

With this endoscopic therapeutic system 96, even when multi-DOF operation is needed, it is possible to achieve effects and advantages similar to those of the prior embodiments.

In addition, the scope of the invention is not limited to any of the above-mentioned embodiments, and various modifications can be made without departing from the spirit of the invention.

For example, in each of the above-mentioned embodiments, in the first mode, both the first forward/reverse mechanism 5 and the second forward/reverse mechanism 6 may be driven to move the sheath section 10 and the operating tube section 11 reversely, but in the first mode, the second rollers 36 which constitute the second forward/reverse mechanism 6 may be made rotatable and only the first forward/reverse mechanism 5 may be driven.

In this case, since only the first forward/reverse mechanism 5 which can be constantly brought in pressure contact with the sheath section 10 may be driven, the first forward/reverse mechanism 5 need not be synchronized with the second forward/reverse mechanism 6, whereby far easier control can be performed. At this time, since the second rollers 36 are made rotatable, tension or compression acting in the axial direction can be prevented from being applied to the sheath section 10 during forward and reverse operations, and the forceps can be prevented from being opened and closed during forward and reverse operations.

Figure 21:
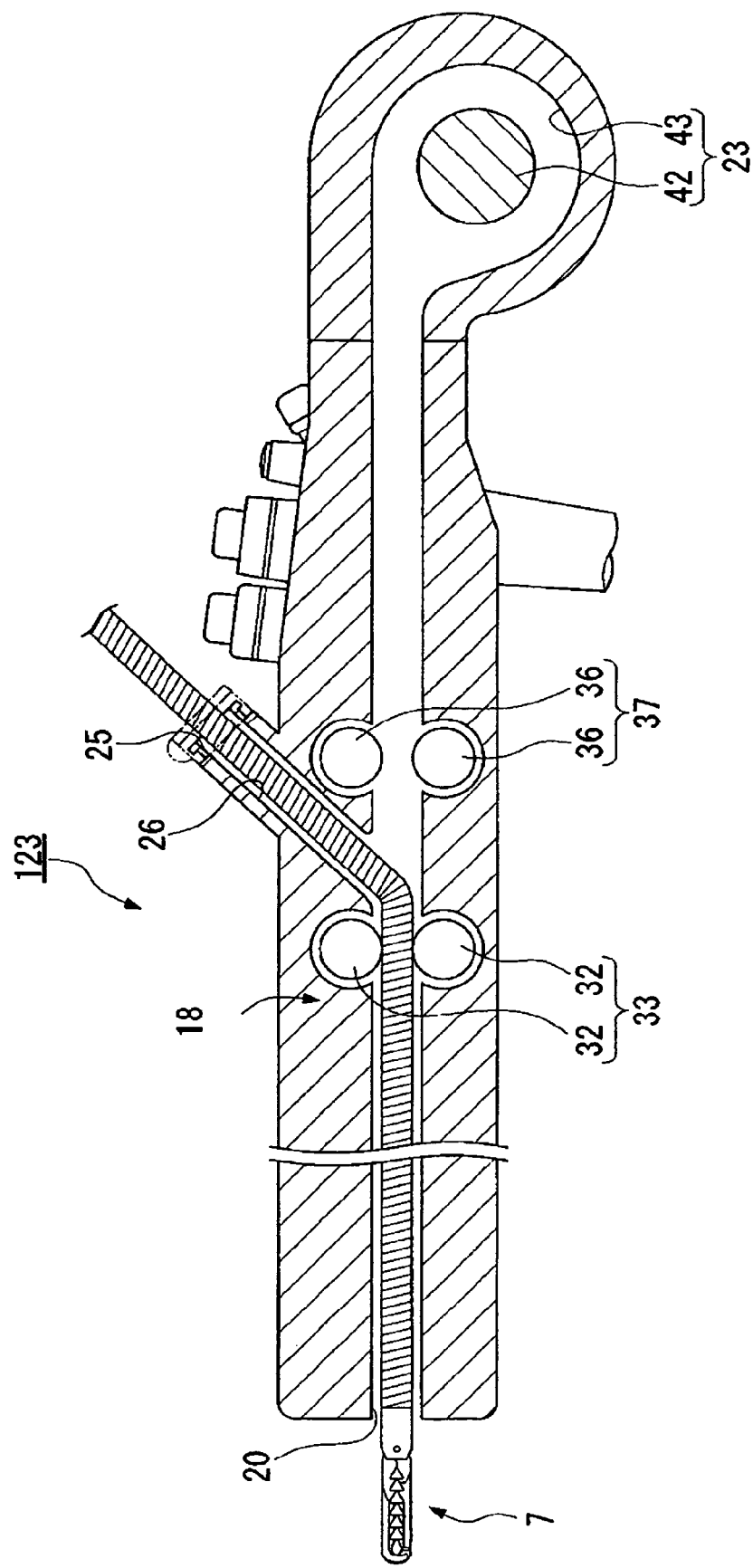
FIG. 21 is a partially cross-sectional side view showing an endoscopic therapeutic system according to another embodiment of the invention.

The first rollers 32 and the second rollers 36 are disposed on a proximal side of the forceps opening 25, but as shown in FIG. 21, in the operating section 18, the first rollers 32 may be disposed on a distal side of the forceps opening 25 and the second rollers 36 may be disposed on the proximal side of the forceps opening 25.

With the endoscopic therapeutic system 123 as well, it is possible to achieve effects and advantages by an operating method similar to that used in the prior embodiments, and even a therapeutic instrument which is provided with a therapeutic instrument operating section like a conventional therapeutic instrument can be operated to move forwardly and reversely in the channel 20, by inserting the therapeutic instrument into the channel 20 from the forceps opening 25 and rotating only the first rollers 32.

Figure 22:
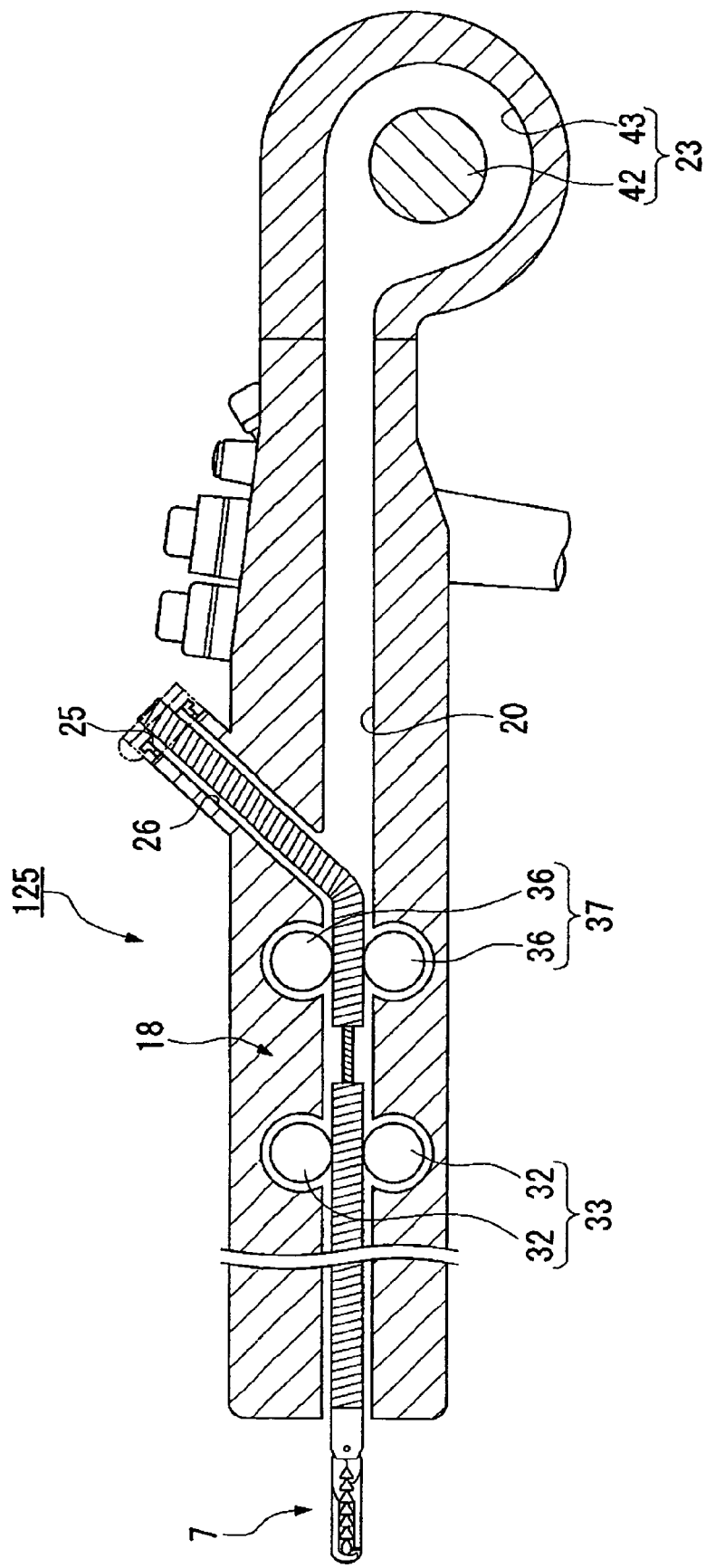
FIG. 22 is a partially cross-sectional side view showing an endoscopic therapeutic system according to another embodiment of the invention.

Furthermore, as shown in FIG. 22, in the operating section 18, the first rollers 32 and the second rollers 36 may be disposed on the distal side of the forceps opening 25.

With this endoscopic therapeutic system 125 as well, it is possible to achieve effects and advantages by an operating method similar to that used in any of the prior embodiments, and even if the forceps is inserted into the channel 20 not from the housing section 23 but from the forceps opening 25, the forceps can be inserted into and removed from the channel 20 and the therapeutic section 7 can be opened and closed.

Figure 23A:
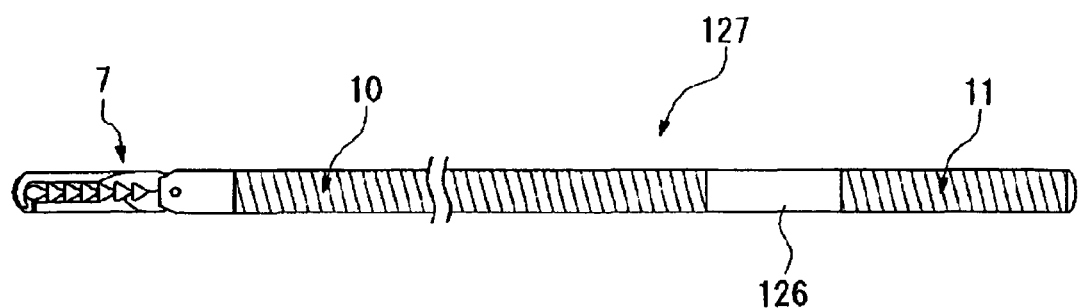
FIGS. 23A and 23B are partially cross-sectional side views showing an endoscopic therapeutic system according to another embodiment of the invention.
Figure 23B:
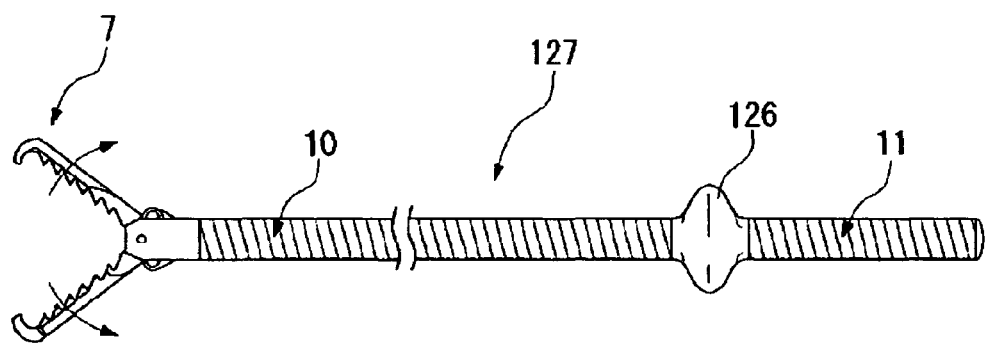
Figure 24A:
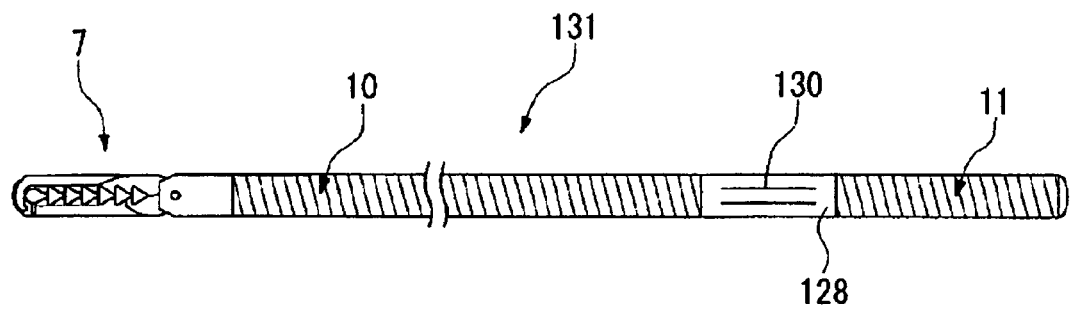
FIGS. 24A and 24B are partially cross-sectional side views showing an endoscopic therapeutic system according to another embodiment of the invention.
Figure 24B:
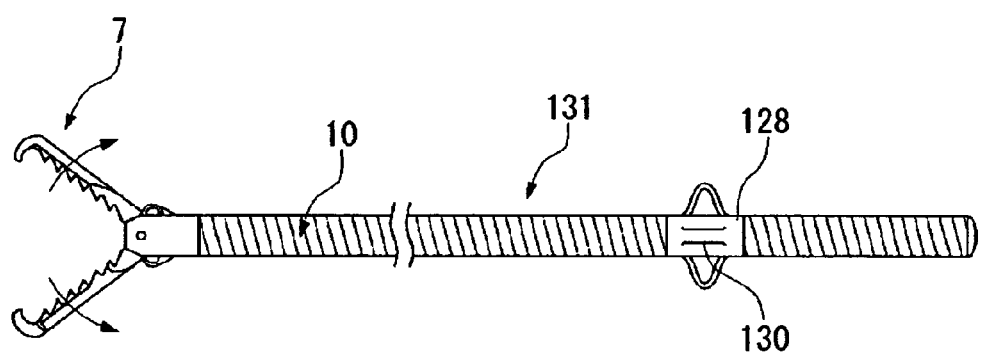

The type of elastic section is not limited to only the spring 50 used in the second embodiment, and the invention may also be applied to a forceps 127 which has an elastic tube 126 made of axially expandable rubber or resin or the like as shown in FIGS. 23A and 23B. In this case, it is possible to obtain effects and advantages similar to those of the second embodiment by means of the deformation of the elastic tube 126. In addition, the invention may also be applied to a forceps 131 shown in FIGS. 24A and 24B which has slits 130 formed to extend along the axial direction of an elastic tube 128 as shown in FIGS. 24A and 24B. In this case, it is possible to deform the elastic tube 128 more flexibly than in the case where the slits 130 are omitted.

While there has been shown and described what are considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. An endoscope system of an endoscopic therapeutic instrument in combination with an endoscope,
   the endoscopic therapeutic instrument comprising:
   a therapeutic section which performs treatment;
   a flexible transmission member which transmits operating driving force to the therapeutic section by moving forwardly and reversely;
   a sheath section defining an interior space in which the flexible transmission member is movable forwardly and reversely; and
   a flexible operating tube section provided separately from the sheath section in an axial direction of the sheath section and connected to a proximate portion of the transmission member which protrudes from the sheath section;
   the system further comprising:
   a channel formed within the endoscope and through which the endoscopic therapeutic instrument is insertable;
   a first forward/reverse mechanism operable to cause the sheath section to move forwardly and reversely within the channel in an axial direction of the channel;
   a second forward/reverse mechanism configured to cause the sheath section and the flexible operating tube section to move forwardly and reversely within the channel in the axial direction of the channel, the second forward/reverse mechanism being independent from the first forward/reverse mechanism;
   a control section operable to control a forward/reverse drive of each of the first and second forward/reverse mechanism, the control section having
      a first mode configured to move the endoscopic therapeutic instrument forwardly reversely by driving both the first and the second forward/reverse mechanisms with the sheath section contacting both the first and the second forward/reverse mechanisms to cause the sheath section to move forwardly and reversely in the axial direction of the sheath section, and
   a second mode configured to operate the therapeutic section by driving one of the first and the second forward/reverse mechanisms with the sheath section contacting the first forward/reverse mechanism and the flexible operating tube section contacting the second forward/reverse mechanism to cause one of the sheath section and the flexible operating tube section to move forwardly and reversely in the axial direction of the sheath section.

2. An endoscope system according to claim 1, wherein: the first forward/reverse mechanism includes a first contact section which contacts with the sheath section and a first feed mechanism which causes the first contact section to feed the sheath section in the axial direction of the sheath; and the second forward/reverse mechanism includes a second contact section which contacts with the operating tube section and a second feed mechanism which causes the second contact section to feed the operating tube section in the axial direction of the sheath.

3. An endoscope system according to claim 2, wherein: the first feed mechanism is a first rotary driving mechanism having a first roller; the first contact section is a peripheral surface of the first roller; the second feed mechanism is a second rotary driving mechanism having a second roller; and the second contact section is a peripheral surface of the second roller.

4. The endoscope system of claim 1, wherein
   the forward movement of the endoscopic therapeutic instrument in the first mode causes the system to transit from the first mode to the second mode.

5. An endoscope system, comprising:
   an endoscope insertion part which is insertable into a body to reach an object which requires treatment, the endoscope insertion part having a channel passing therethrough;
   a flexible tube slidingly disposed in the channel and having a treatment tool attached to a distal portion thereof;
   a control wire slidably disposed in the flexible tube and having a distal end coupled to the treatment tool and having a proximate end which is attached to a flexible handle;
   the flexible handle and the control wire attached thereto being slidable back and forth along an axial direction of the flexible tube; and
   first and second drive mechanisms and a controller configured to control the first and second drive mechanism to operate in a first mode and in a second mode, wherein in the first mode both drive mechanisms engage and drive only the flexible tube and in the second mode the first drive mechanism engages and drives the flexible tube and the second drive mechanism engages and drives the flexible handle.

6. The endoscope system of claim 5, including a storage facility having an interior which is in communication with the channel of the endoscope, the flexible tube, the flexible handle and the wire attached thereto being moveable to be stored within the storage facility.

7. The endoscope system of claim 6, in which the storage facility has a core on which the flexible tube and the flexible handle are windable.

8. The endoscope system of claim 6, wherein the storage facility has a spiral construction in which the flexible tube and the flexible handle are receivable.

9. The endoscope system of claim 5, wherein each of the first drive and the second drive comprises respective rollers which frictionally engage a respective one of the flexible tube and the flexible handle to drive the same by rotational movement thereof.

10. The endoscope system of claim 5, further including a forceps opening in the endoscope insertion part provided at the proximal side of the endoscope insertion part, which endoscope forceps opening is in communication with the endoscope channel for inserting into the channel an object treating instrument.

11. The endoscope system of claim 10, wherein the forceps opening provided at the proximal side of the endoscope insertion part has an entry location into the channel which is located closer to a distal end of the channel than the first and second drives.

12. The endoscope system of claim 5, wherein the flexible tube comprises first and second sections and wherein the first drive comprises a first roller pair and a second roller pair corresponding, respectively, to the first section and the second section.

* * * * *